US010335269B2

(12) United States Patent
Fahl

(10) Patent No.: US 10,335,269 B2
(45) Date of Patent: Jul. 2, 2019

(54) SPEAKING VALVE HAVING A COVER PART FORMED AT LEAST PARTIALLY OF AN ELASTIC MATERIAL

(71) Applicant: Andreas Fahl Medizintechnik—Vertrieb GmbH, Cologne (DE)

(72) Inventor: Andreas Fahl, Köln (DE)

(73) Assignee: Andreas Fahl Medizintechnik—Vertrieb GmbH, Cologne (DE)

( * ) Notice: Subject to any disclaimer, the term of this patent is extended or adjusted under 35 U.S.C. 154(b) by 0 days.

(21) Appl. No.: 15/238,966

(22) Filed: Aug. 17, 2016

(65) Prior Publication Data
US 2016/0354199 A1 Dec. 8, 2016

Related U.S. Application Data

(63) Continuation of application No. PCT/EP2015/000315, filed on Feb. 13, 2015.

(30) Foreign Application Priority Data

Feb. 18, 2014 (DE) ........................ 10 2014 002 063

(51) Int. Cl.
*A61F 2/20* (2006.01)
*A61M 16/04* (2006.01)
*A61M 16/10* (2006.01)

(52) U.S. Cl.
CPC ........... *A61F 2/20* (2013.01); *A61M 16/0468* (2013.01); *A61M 16/1045* (2013.01);
(Continued)

(58) Field of Classification Search
CPC ...... A61F 2/20; A61F 2002/206; A61F 2/203; A61M 16/04; A61M 16/0468; A61M 16/047; A61M 16/1045; A61M 6/0468
See application file for complete search history.

(56) References Cited

U.S. PATENT DOCUMENTS

| 4,582,058 A | 4/1986 | Depel et al. |
| 2003/0029456 A1* | 2/2003 | Lambert ........... A61M 16/0468 128/207.15 |

(Continued)

FOREIGN PATENT DOCUMENTS

| DE | 102005007234 B3 | 7/2006 |
| DE | 102010048317 A1 | 4/2012 |

(Continued)

OTHER PUBLICATIONS

International Search Report dated Jul. 2, 2015, International Application No. PCT/EP2015/000315, filed Feb. 13, 2015.

*Primary Examiner* — Andrew M Iwamaye
(74) *Attorney, Agent, or Firm* — Dinsmore & Shohl LLP

(57) ABSTRACT

In order to solve the problem of providing a speaking valve which is of simple construction and which is inexpensive to produce, a speaking valve (1) is proposed which has a cover part (2), a controller (3), a housing part (5) and a filter (8), wherein the housing part provides a valve seat arranged proximally therein, wherein the controller comprises a closure part (4), and wherein the closure part cooperates with the valve seat when the speaking valve is moved from an open position into a closed position, wherein the cover part is formed at least partially of an elastic material, wherein an at least partial deformation of at least one region of the cover part takes place as a result of the speaking valve being moved from the open position into the closed position, and wherein the filter is arranged on the controller in such a way that the filter can substantially follow the movement of the controller.

17 Claims, 4 Drawing Sheets

(52) U.S. Cl.
CPC .............. *A61F 2250/0018* (2013.01); *A61F 2250/0024* (2013.01); *A61F 2250/0029* (2013.01)

(56) References Cited

U.S. PATENT DOCUMENTS

2012/0090621 A1* 4/2012 van der Houwen .......................... A61M 16/0468
128/207.16
2013/0192602 A1* 8/2013 Leibitzki .......... A61M 16/0468
128/205.27

FOREIGN PATENT DOCUMENTS

| DE | 202012001825 U1 | 4/2012 | |
|---|---|---|---|
| DE | 202013008092 U1 | 10/2013 | |
| DE | 20 2013 008 092 | * 12/2013 | ............ A61M 16/10 |
| EP | 1077658 A1 | 2/2001 | |
| EP | 2236165 A1 | 10/2010 | |
| WO | 9517138 A1 | 6/1995 | |
| WO | 9960954 A1 | 12/1999 | |
| WO | 2011144237 A1 | 11/2011 | |

* cited by examiner

SPEAKING VALVE HAVING A COVER PART FORMED AT LEAST PARTIALLY OF AN ELASTIC MATERIAL

CROSS-REFERENCE TO RELATED APPLICATIONS

This application is a continuation of PCT/EP2015/000315 filed Feb. 13, 2015, which claims priority of German Patent Application 10 2014 002 063.0 filed Feb. 18, 2014.

FIELD OF THE INVENTION

The invention relates to a speaking valve for laryngectomy or tracheostomy care having a cover part, a controller, a closure part, a housing part and a valve seat arranged in the housing.

BACKGROUND OF THE INVENTION

Speaking valves are well-known in prior art. For example, they are attached to a tracheostomy tube or tracheostomy patch, so that people without vocal cords can speak by means of a voice prosthesis. By activating the speaking valve, air is guided through a voice prosthesis, which is arranged in a fistula between the trachea and the esophagus. Even if the vocal cords are still available, it is important that the air does not escape from the tracheal tube before it reaches the vocal cords.

From U.S. Pat. No. 4,582,058A it is known to close a speaking valve by means of a pressure impulse effected by the patient's breathing, thus allowing the person to speak. However, these valves proved to be not very reliable.

WO 95/17138 A proposes to combine the speaking valve with an artificial nose. This artificial nose is a filter which absorbs moisture and heat from the exhaled air and which moistens and heats the air streaming into the tracheal tube.

EP 1 077 658 B1 describes a vocal valve having a filter, wherein the vocal valve comprises an elastic housing or elastic valve element and the housing or valve element can be deformed, for example, by means of finger pressure, in such a way that a housing part is pushed on a valve seat and the valve is closed.

SUMMARY OF THE INVENTION

It is the object of the present invention to provide a speaking valve, which has a simple design and which can be produced in a cost-effective manner.

According to the invention, this object is achieved by means of a speaking valve according to claim 1. Further advantageous embodiments are included in the following description, the figures and the sub-claims. However, the embodiment is not restricted to the individual properties described but can be combined with one another, as well as with other properties.

The invention proposes a speaking valve for laryngectomy or tracheostomy care, wherein the speaking valve has a cover part, a controller, a housing part and a filter. The housing part provides a valve seat arranged proximally therein. The controller comprises a closure part, wherein the closure part cooperates with the valve seat when the speaking valve is moved from an open position into a closed position in order to allow for speaking. The cover part is formed at least partially of an elastic material. An at least partial deformation of at least one portion of the cover part takes place as a result of the speaking valve being moved from the open position into the closed position. The filter is arranged on the controller in such a way that the filter can basically follow the movement of the controller, and preferably does follow the movement of the controller. The proximally arranged valve seat is designed to be close to the body or closer to the body than a distal opening of the speaking valve, which is located above the proximally arranged valve seat. At the same time, the proximally arranged valve seat can be formed, for example, by a base plate designed in the form of a ring, or by a preferably circular surface, which is provided at the wall of the housing. Provision can also be made for a proximal opening consisting of wall components protruding into the interior of the housing, based on a base ring, allowing the speaking valve to be placed on a 15 mm tracheal tube. The wall components can be described, for example, as forming a socket. Such combination valves can be designed in the form described in DE 10 2005 007 234 B3. The valve seat is not formed by the wall components mentioned. The resetting forces, which are required when the speaking valve is moved from a closed position, necessary for speaking, into an open position, are mostly, or even completely provided by the cover part, which is formed of elastic material. This is of advantage because it eliminates resetting means such as springs or the like that would otherwise be required. Since the filter is only minimally, or preferably not at all compressed because it is carried along, its function of heat and moisture exchange is virtually, if not completely maintained.

According to the present invention and in relation to a property of the invention-based device, the term "distal" refers to an arrangement or use of the device remotely from or facing away from or opposite from a tracheostomy patch or tracheal tube, more general a skin surface of a person which, in particular, has such mounting components for the invention-based device. According to the present invention and in relation to a property of the invention-based device, the term "proximal" refers to an arrangement or use of the device close to or facing or adjacent to a tracheostomy patch or tracheal tube, more general a skin surface of a person which, in particular, has such mounting components for the invention-based device.

When the present invention gives directional information, this is to be understood always in relation to an installation for the designated use of the speaking valve on the body. According to its designated use, the invention-based speaking valve is placed above the tracheostomy and, in particular, mounted on a tracheal tube or tracheostomy patch.

When the present invention uses the term "basically", it provides a tolerance range which, for an expert, involves economic and technical aspects, so that the respective property can still be recognized and fulfills the intended function.

Advantageously, the cover part is designed in the form of a hat or cap. This involves a design of the cover part in which the cover part overlaps at least partially, preferably completely (i.e., on all sides), a sidewall of the housing part. Advantageously, the overlapping of the sidewall of the housing part takes place in one direction, basically parallel to a skin surface of the body. Furthermore, the overlapping of the sidewall of the housing part takes place vertically, i.e., in the direction of the vertical extension of the housing part, from its proximal end to its distal end. Preferably, the vertical overlapping takes place via a partial length of the vertical extension of the housing part. In the portion overlapping the sidewall of the housing part, the cover part can also have openings, in particular slot-shaped openings.

From proximal to distal, in relation to the end portions of the housing part, the cover part advantageously comprises a height, which corresponds at least to between 30% and approximately 95%, preferably between approximately 40% and approximately 95%, more preferred between approximately 50% and approximately 95%, even more preferred between approximately 70% and approximately 95%, still more preferred between approximately 80% and approximately 90% of a height of the housing part. Preferably, the housing part comprises from proximal to distal a height, which is maximally approximately 95%, more preferred maximally approximately 90%, even more preferred maximally approximately 80% of the height of the housing part, calculated based on the proximal lower edge of the sidewall of the housing facing the body to the distal upper edge of the sidewall of the housing facing away from the body.

The height of the cover part from proximal to distal is determined by the cervical edge, on the one hand, and by the distal surface of the cover part, on the other hand, which extends furthest from the tracheostomy.

When, in the context of the present invention, the term "approximately" is used, it refers to a tolerance range, which an appropriate expert in the field would consider normal, especially a tolerance range of +/−20%, preferably +/−10%, more preferred +/−5%, respectively, in relation to the value in question, in relation to the values mentioned.

In a preferred embodiment, the cover part overlaps the housing laterally, as well as vertically. More preferred, the cover part comprises a cervical edge. The cervical edge, which is facing the neck of a wearer of the invention-based speaking valve, has preferably a rounded design, thus avoiding skin irritations when a skin contact takes place as a result of movements of the user. In particular, from a lateral top view, the cover part has an oval or otherwise rounded or rectangular design, wherein with a rectangular design, the edges would preferably be rounded.

The advantage of each of the properties described above in the context of the design of the cover part is that when inhaling the air is guided along the neck, which results in the fact that the air is preheated before it reaches the interior of the speaking valve and especially the filter. Depending on the design of the cover part, especially with regard to arranging the cervical edge rather close to the sidewall of the housing part or rather remotely from said sidewall, as well as arranging the cover part with the cervical edge in such a way that the cervical edge is arranged close to or spaced further away from the neck of the user, it is possible to adjust the volume of the airflow to be absorbed and the preheating process of the airflow.

To this end, it is of special advantage when, especially in a central portion facing the cover part, the cover part has no distal opening which allows for an airflow from distal to proximal through the filter. Then the housing part preferably comprises one or multiple inflow openings in a sidewall of the housing part. As a result, the air is basically guided along the neck before entering the housing part. However, alternatively or additionally, it can also be provided that the cover part has at least one distal opening, especially in a portion facing the interior of the housing part. By means of the at least one distal opening, at least a portion of the inhaled air can enter the housing or penetrate the filter, so that the air is moistened and heated when entering the trachea or the tracheal tube.

Preferably, the cover part is detachably connected with the housing part and/or the controller. It is preferred when the cover part is detachably connected with the housing part and firmly connected with the controller. In another preferred embodiment, the cover part is detachably connected with the housing part and detachably connected with the controller.

The detachability especially of the controller is preferably impeded compared to the detachability of the cover part. In the last-mentioned embodiments, the cover part together with the controller and the attached filter form one component of the invention-based speaking valve, the other component is formed by the housing part. The cover part can form a single piece with the controller. Advantageously, the cover part can be attached to the housing part by means of a snap-on connection. Other possibilities for a detachable connection can also be provided, for example, one or multiple Velcro connections or adhesive bonds. The snap-on connection can be performed in such a way that the cover part comprises two, three, four or more snap-on elements, for example, in the form of lugs, which are arranged on an inner surface of the cover part, attached to the sidewall. At the same time, it can be provided that the snap-on elements surround an upper edge of the housing part in a region in which inflow openings are provided. On this edge, respective receiving spaces or recesses or cut-outs can be provided into which the snap-on elements of the cover part are engaging. Conversely, respective snap-on elements can also be arranged at the distal end portion of the housing part, for example, lugs, which engage into respective recesses arranged at the bottom side of the cover part. Preferably, the detachable connection between cover part and housing part is designed in such a way that in the connection space no air can stream in or out between the cover part and the housing part. For example, it can be provided that three or four lugs and/or recesses are arranged on the inner side of the cover part. To obtain a sufficiently firm connection, these lugs and/or recesses are arranged on a band or bulge, which is located on the inner side of the cover part and which corresponds in dimension, in particular in its diameter, to the diameter of the housing part and covers or overlaps the upper edge of the sidewall of the housing part. Preferably, the snap-on elements or lugs engage into respective recesses at the upper edge of the cover part. Conversely, lugs at the upper edge of the cover part can engage into the recesses. At the same time, the bulge or band can be arranged in such a way that it is only minimally spaced from the cervical edge of the cover part, insofar as the cover part overlaps only the sidewall of the housing part. However, the cover part can be riveted or screwed to the housing part, or it can be connected with the housing part by means of a bayonet coupling.

According to the invention, the cover part is formed at least partially of an elastic material. Advantageously, the elastic material of the cover part consists of a rubber-elastic material. Preferably, the elastic material of the cover part is a linear-elastic material. In particular, the rubber-elastic material to be used can consist of natural rubber or synthetic rubber, especially butyl rubber or ethylene-propylene-diene rubber (EPDM). However, it is also possible to use silicone materials, in particular medical silicone materials. In principle, the rubber-elastic material of the cover part can consist of an elastomer, for example, a thermoplastic elastomer on an olefin or urethane basis, especially preferred an at least partially cross-linked thermoplastic elastomer on an olefin basis, a polyester elastomer, a thermoplastic copolyester, a styrene block polymer or a thermoplastic copolymer. Instead of being produced from a rubber-elastic material, the cover part can also be formed, at least partially, of a linear-elastic material, especially a metal, which provides sufficient elasticity. But it is also possible to use other materials, which provide sufficient elasticity. Especially preferred, the cover part consists of an elastic, preferably rubber-elastic material and therefore does not comprise any other material. At the same time, the cover part can have a uniform thickness.

However, especially in the region of the transition from a horizontal to a vertical extension of the cover part, the thickness can be reduced, and/or also in a region in which the user can move with his finger the speaking valve from the open position into the closed position and back.

In a preferred embodiment, at least one flexibly deformable region of the cover part functions as a resetting means for moving from the closed position into the open position. Finally, through the elasticity of the cover part, a return from the closed position into the open position of the speaking valve is achieved in that a force in the direction of the tracheostomy is exerted via the cover part and, as a result, the closure part comes into an operative connection with the valve seat in order to close the speaking valve by releasing or removing, for example, the finger of the user, which was used to close the speaking valve. As a result, it is again possible to breathe through the speaking valve. This function is performed by the cover part as a whole or by a portion of the cover part. For example, the cover part can also be designed in such a way that it comprises an elastic region where the cover part is facing the interior of the housing part, which is then connected to a less flexible region or even to an inflexible region, in which the previously mentioned snap-on elements are arranged on the inner wall of the cover part. When the outer surface overlaps the sidewall of the housing part, i.e., when in particular the cover part is designed in the form of a hat or a cap, this overlapping region can be produced also from a sufficiently firm material. Then, the cervical edge or edge region can be produced, for example, from a soft material, for example, silicone, in order to avoid skin irritations. It can also be provided that in the region facing the interior of the housing part, the cover part is formed of a linear-elastic material, for example, an appropriate metal to which a sufficiently flexible elastic plastic material is connected when provision has been made that the exterior side of the outer wall of the housing part is overlapping. In an embodiment having a cover part which has at least one elastic region facing the interior of the housing part, it is possible for attaching the controller to provide a reinforced region in the form of a material build-up, especially in the form of a ring, into which the controller can be inserted via appropriate mounting components. But it is also possible to use any other embodiment of a cover part, provided it performs the function of serving of a resetting means when moving the invention-based speaking valve from the closed position into the open position.

Advantageously, the housing part comprises at least one inflow opening in its sidewall. Preferably, multiple inflow openings can be provided, in particular three, four, five or six or even more. At the same time, the housing part can have, at least partially, a frame-like design. In the frame-like region, inflow openings are arranged, wherein basically only bars are arranged between the inflow openings, which connect a lower proximal end portion of the speaking valve with an upper end portion, especially an end portion designed in the form of a circumferential ring. Advantageously, the bars function as a support for the filter. In this way, it is also possible, at least indirectly, to guide the controller in the interior of the housing part when moving from the open position into the closed position and vice versa. The inflow openings should be designed as large as possible. Preferably they occupy between approximately 30% and approximately 90%, more preferred between approximately 40% and approximately 90%, even more preferred between approximately 40% and approximately 85% of the sidewall. The inflow openings can have any geometry, for example, the inflow openings can have a sieve-like design. By providing a large region for the inflow openings in the sidewall of the housing part, a large air passage can be obtained.

Advantageously, at its proximal end, the housing part comprises an opening for a connection with the tracheostomy. This opening is arranged in a base of the housing part. Preferably, the base is formed by a circumferential circular edge, which is arranged at the sidewall, wherein advantageously bars are used for reinforcement, which are arranged in cross-like manner within the region formed by the circular edge of the base and connected with the circular edge. A surface of the circular edge of the base, at least a portion of it, is used as a valve seat for the invention-based speaking valve and can comprise in this region a support consisting of an appropriate material in order to achieve the best possible sealing effect. For example, in the respective regions a medical silicone or any other suitable sealant can be arranged. When providing a cross-shaped base in the form of three, four, five or more bars, a guiding device for the controller can be provided at the point of intersection of the bars, which protrudes into the interior of the housing part. For example, said guiding device can have a rod-shaped design. Preferably, it engages into a recess of the controller situated in the closure part and/or connection part of the controller, which connects the closure part with the cover part to allow the controller to move via the cover part. For example, the recess can be provided by means of a tubular connection, which is at least on one side proximally open. It is possible to engage a rod-shaped guiding device into the recess.

In the distal end portion of the housing part, lugs or other snap-on elements can be provided in order to arrange for a detachable attachment with the cover part. In particular, these lugs or snap-on elements are arranged at a circumferential ring. Additionally, or alternatively, said ring can also be provided with recesses or cut-outs, into which snap-on elements, which are arranged at the inner wall of the cover part and facing the housing part, can be engaged or received.

Advantageously, at least one inflow opening in the sidewall of the housing part has a lateral expansion which corresponds to up to a height of the controller and/or to approximately a height of the filter. Advantageously, the lateral expansion of the inflow opening is selected in relation to a filter arranged at the controller in the interior of the housing part in such a way that the filter somewhat overlaps the proximal and/or distal end of the inflow opening, preferably the proximal end, to ensure that the inhaled airflow passes the filter as completely as possible.

The distal end of the housing part comprises a distal opening through which the controller with the filter body can be inserted into the interior of the housing. At the same time, it is possible to guide an airflow also via this distal opening in the housing part, provided respective openings have been provided in the controller and/or cover part. Naturally, these distal openings in the controller and/or cover part have to be designed in such a way that they can be hermetically closed when the user activates the speaking valve, which is usually done with a finger.

Advantageously, the housing part is formed of a rigid, i.e., inflexible or bend-resistant material, for example, a suitable polyethylene or polypropylene, in particular a high-density polyethylene (HDPE).

Preferably, the filter comprises an open-cell foam which, in particular, is antimicrobial. For example, coated with silver or the like. The filter can also be impregnated with specific materials in order to increase moisture absorption. Advantageously, when the filter is made out of foam material, it comprises at least a material of polyester, polyethylene and/or polyurethane. However, any other material can also be used for producing the filter, for example, it can be produced from paper or metal. Preferably, the filter carries out a heat exchange and/or moisture exchange function in the manner of prior art described at the outset. Preferably, the filter is not or only slightly compressed when the speaking valve is activated.

According to the invention, the controller comprises the closure part, which cooperates with the valve seat provided by the housing part. According to the invention, the filter is arranged at the controller in such a way that it can basically follow the movement of the controller. The movement of the controller is carried out when a user moves the speaking valve from the open position into the closed position and, because of providing an elastic material in the cover part, when the speaking valve is reset from the closed position into the open position. Advantageously, the filter remains basically uncompressed when the speaking valve is moved from the open position into the closed position, as well as from the closed position into the open position. For example, this can take place when above the filter body a mounting element of the cover part is provided at the distal end of the controller, which mounting element is basically designed in the form of a plate. Then, the filter body can be arranged between the closure part and the cover part of the mounting element of the controller. As a result, the movement of the controller can be carried out via the region of the mounting element of the cover part. At the same time, the filter can be glued or otherwise connected to the closure part and the cover part and/or the mounting element of the cover part. However, the controller can also be designed in such a way that a connection piece is provided between the closure part and the mounting element of the cover part and/or cover part. Said connection piece is designed in the form of a rod or wall to provide the controller with sufficient strength. When viewed in cross section, the provision of a mounting element of the cover part gives the controller a single T-shaped or double T-shaped design. By not compressing the filter, which can be achieved by means of the previously described exemplary embodiment of the controller, it is not only possible to prevent a violation or any other infringement of the function of the filter, but it can also be prevented that a large amount of moisture absorbed in the filter is discharged at once when the invention-based speaking valve is activated. For example, the connection piece, which connects the closure part and the cover part, possibly via the mounting element of the cover part of the controller, can be formed by two crossing wall components, which may or may not have openings. In this case, depending on the dimensions of the walls, a four divisional filter could be arranged at the controller. For example, if the connection piece is designed in tube, rod or pole-shaped manner, it is possible simply to insert a one-piece filter with a drill hole in the region of the connection piece. If the connection piece is simply designed in the form of a wall, which extends across the entire diameter of the closure part, a two-piece filter can be inserted. The cover part can also be connected with a controller, which has only a closure part and a connection piece. For example, the connection space between connection piece and cover part in the cover part is then formed by a more rigid, preferably only slightly flexible or inflexible material. At the same time, the controller and the cover part can be connected via the means of connection in detachable or non-detachable manner. A detachable design is preferred, however, the detachability is to be impeded. For example, in the center of the mounting area on the bottom side of the cover part, a material build-up is provided, for example, in the form of a ring with a central opening into which the end of the expanded connection piece located opposite of the closure part can be snapped. Cover part and controller with the closure part can also be designed in one piece, for example by forming a bond with the filter located in between. However, it is also possible to design the controller with closure part and cover part from the same material. Preferably, though, the cover part is formed at least partially, preferably completely, from an elastic material and the controller from a rigid material, which, as described below, can also be used for the housing part.

Preferably, the filter is designed in such a way that its outer wall is attached to an inner wall of the housing part. However, it can also be provided that the outer wall of the filter facing the inner surface of the sidewall of the housing part is spaced from said inner surface of the sidewall, thus forming a gap. However, the filter can also be dimensioned in such a way that it is proportioned in the housing part in a press-fitting manner. When the speaking valve is activated, preferably no further compression occurs beyond this press-fitting, which corresponds to a partial compression. This press-fitting process results in a fixation of the filter so that is cannot be moved when the cover part is activated. This depends also on the dimensions of the receiving space of the filter in the housing part, wherein, depending on the clearance between the closure part and the bottom of the housing part, the filter can follow the controller, provided sufficient force is available. It also depends on the force exerted on the press-fitting. With light force, the filter can be moved easily.

The closure part of the controller can have different designs. On the one hand, the closure part has to fulfill the function of achieving a sufficiently tight seal with the valve seat provided by the housing part. On the other hand, the closure part has to be dimensioned in such a way that sufficient air can flow via the filter in or out of the tracheostomy. For example, for this purpose it can be provided that in the housing part the proximal opening is designed considerably smaller than the distal opening, so that the closure part has a smaller diameter than the mounting element of the cover part. This results in a turntable design of the closure part. When now the speaking valve is moved from the open position to the closed position, the edge region of the speaking valve forms an interactive connection with the valve seat formed by the bottom of the housing part and the opposite circumferential edge in order to interrupt the airflow. In this embodiment, the filter can be designed in such a way that the outer wall of the filter, which faces the sidewall of the housing part, overlaps the closure part horizontally and therefore has a larger diameter than the closure part. However, depending on the dimensions of the speaking valve, an adequate airflow in and out of the tracheostomy can be provided even with a maximum diameter of the closure part and a design in the form of a turntable, as long as a gap is provided between the outer wall of the filter body and the inner surface of the sidewall and, correspondingly, between the sidewall and the closure part. Insofar as the closure part of the controller cooperates with the valve seat to achieve an adequate sealing effect, said closure part can also have openings in the horizontally extending portion overlapping the valve seat, through which inhaled or exhaled air can flow. For example, it can also be provided that the closure part, as well as the mounting element of the cover part have a small diameter at the distal end of the controller, i.e., a diameter which is considerably smaller than the inner diameter of the housing part, whereas the filter has a larger diameter, especially one that basically corresponds to the inner diameter of the housing part or, when press-fitting is provided, it is even larger, so that the filter body is attached via its outer wall to an inner surface of the sidewall of the housing part. However, the mounting element of the cover part, if available, and the closure part may or may not have different diameters.

Preferably, the controller is produced from a rigid, in particular inflexible or bend-resistant material, such as polyethylene or polypropylene, especially high-density polyethylene (HDPE). Especially when designed as one piece with the cover part, it can also consist of the above-mentioned materials used for the cover part.

Advantageously, the controller is arranged at the cover part. This arrangement can be made in different ways. For example, when the cover part is designed without a mounting element, the arrangement of placing the controller on the cover part can basically occur via the filter, wherein then the cover part is connected with the filter by means of adhesion, interlocking or any other means. In such an embodiment when the cover part is designed without a mounting element, the controller preferably comprises a connection piece in the form of a rod or a wall or any other form, as described above, in order to achieve sufficient strength. In particular, said connection piece transfers the forces applied when moving the speaking valve from an open position into a closed position to the closure part in order to achieve an operative connection with the valve seat, with the valve seat provided by the housing part.

Preferably, the cover part is connected with the mounting element of the cover part of the controller. For example, the proximal bottom part (inner wall) of the cover part can be connected with a distal surface of the mounting element of the cover part. The connection can be made in any form, for example, by means of adhesion, Velcro, screw connection or catch mechanism. Especially preferred is a catch mechanism or adhesion. It can also be provided that the mounting element of the cover part is connected with the cover part in such a way that, at a central opening of the cover part, an inner edge of it is connected with an outer edge of the mounting element of the cover part. For example, the cover part can be arranged completely or partially above the mounting element of the cover part, so that it is invisible from the outside. It is possible to provide retaining elements, which are guided through an opening from above the cover part and which are attached at least partially to the inner wall of the cover part. The retaining element can be designed in the form of a spring arm. In addition, it is possible to provide distally located openings in the cover part or mounting element of the cover part to achieve an air passage. Then it is not necessary to provide inflow openings in the sidewall of the housing part but, if desired, they can be provided. Cover and controller can be produced in one piece. Preferably they are produced in the form of a one-component injection molding. It is preferred that they are produced from the same material, preferably an elastic material from which the cover part is produced. By reinforcing the wall thickness or with the use of other mechanical means, for example, strengthening ribs, corrugations, hollow spaces or the like, the controller can be provided with greater rigidity and reduced elasticity. It is also possible to produce two-component injection molding, using an elastic material for the cover part and a different material for the controller, which may be flexible or rigid.

According to the present invention, the controller comprises at least the closure part, preferably also the mounting element of the cover part, and a connection piece of the invention-based speaking valve. As described above, the connection piece connects the mounting element of the cover part or the cover part with the closure part. Together with the valve seat, which is provided by the housing part, the controller, more precisely its closure part, forms the valve element of the invention-based speaking valve. Preferably, the controller is only connected with the cover part, and more preferred the cover part only with the housing. Then the cover part forms one unit with the controller, which is inserted into the housing part. At the same time, the cover part assumes the function of resetting means and provides adequate elasticity for closing the valve element. In the interior of the housing part, the controller is guided via an alignment by the cover part, which is preferably connected with the housing part via snap-on connections. A more extensive guidance can be achieved when, in particular, the outer wall of the filter is attached to the inside of the sidewall of the housing and the filter is accepted in a press fit in the housing part. Moreover, the guidance can also take place via the sidewall of the closure part, if the diameter of the closure part is approximately adapted to the inside diameter of the housing part.

BRIEF DESCRIPTION OF THE DRAWINGS

This advantage, as well as other advantages of the present invention are described in more detail by means of the following embodiment. It is shown.

DETAILED DESCRIPTION OF THE PREFERRED EMBODIMENTS

Figure 1:
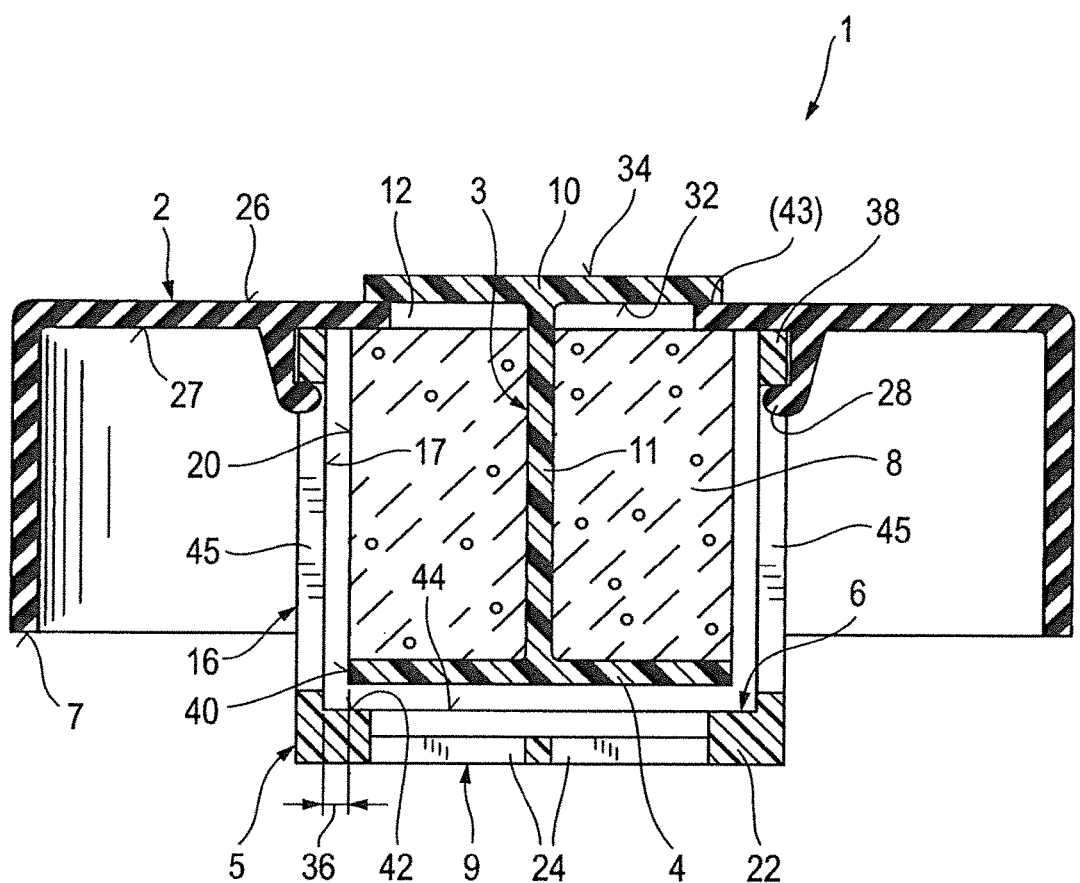
FIG. 1 a lateral sectional view of a speaking valve in open position.

First of all, it should be noted that the embodiments shown in the figures represent only examples and should not restrict the scope of protection of the present invention. In particular, the embodiments shown in the figures can be combined with the properties described above in the general description to form further embodiments. In particular, it should be noted that the demonstrated connection between cover part and housing part, as well as between cover part and controller represents only one of the possible embodiments. In the same way, the embodiment of the controller arranged with filter and closure part, which shows a gap between an inner surface of a sidewall of the housing part and a side edge of the closure part represents only an example. Also the shape of the cover part is only one of the possible diverse embodiments of the cover part which, in particular, can be designed in the form of a hat or cap, having a cervical edge, which is facing the skin surface of a user. The proximally arranged valve seat is provided not by the bottom of the housing but, for example, by a recess in the housing wall, thus forming there a circular surface. As a result, the proximally arranged valve seat is further removed from the body of the user but still closer than to at least one distal opening of the speaking valve.

It should be further noted that the reference numerals mentioned in the description of the figures do not restrict the scope of protection of the present invention but only make reference to the embodiments shown in the figures.

FIG. 1 shows a speaking valve 1 which can be put on a tracheostomy tube (not shown) or tracheostomy patch (not shown). The speaking valve 1 comprises a cover part 2, a controller 3, a housing part 5 and a filter 8. The cover part 2 overlaps the housing part 5 laterally and vertically and has, in particular, a cervical edge 7. It is basically designed in the form of a hat or cap and has an approximately oval shape when viewed from the top. The cover part 2 has a distal exterior 26 and a distal bottom side 27. The cover part is put on the housing part 5 in cap-like manner and is connected with the housing part via snap-on elements, designed in the form of lugs 28. These lugs 28 engage into an upper edge 38 of the housing part 5, as well as recesses provided there. In the embodiment shown, the recesses are also inflow openings 45. Preferably, four lugs 28 are provided, which are arranged at the bottom side 27 of the cover part 2. The cover part 2 is completely produced from rubber-elastic material. The cover part 2 has a distal opening 12, which is provided for receiving a mounting element 10 of the cover part of the controller 5. Advantageously, the mounting element 10 of the cover part closes the distal opening 12 of the cover part. At the same time, the mounting element 10 of the cover part can comprise openings, which are closed when the speaking valve 1 is moved from an open position into a closed position, for example, with the finger of the user. According to an alternative embodiment, an edge region of the bottom side 32 of the mounting element 10 of the cover part can be firmly connected by means of adhesion 43 with the exterior 26 of the cover part 2.

In addition to the mounting element 10 of the cover part, the controller 3 also comprises a connection piece 11, which has a tube or rod-shaped design, and the mounting element 10 of the cover part with a closure part 4, which is arranged close to a proximal opening 9 of the housing part 5. The connection piece 11 extends through the filter 8, which is designed in one piece and has an outer wall 20, which is spaced from an inner surface 17 of a sidewall 16 of the housing part 5. The diameter of the filter 8 basically corresponds to the diameter of the mounting element 10 of the cover part and the closure part, so that a gap 36 is formed between a lateral edge 40 of the closure part 4 and the inner surface 17 of the sidewall 16 of the housing part 5 and a gap 36 is formed between the outer wall of the filter 8 and the inner surface 17 of the sidewall 16 of the housing part 5.

The closure part 4, which is designed in the form of a turntable, cooperates with a valve seat 6 when the speaking valve 1 is closed. The valve seat 6 is formed by a portion of the base 22, which is formed by a circumferential edge 44 and a cross of connection bars 24 formed by three, four or more arms and arranged for reinforcement inside the opening 9. A surface 42 of the circumferential edge 44 forms in part the valve seat 6.

The housing part 5 has inflow openings 45, which are located in the sidewall 16 of the housing part 5. The inflow openings 45 have a lateral expansion which approximately correspond to the height of the filter 8. In particular, the inflow openings 45 are arranged in the sidewall 1 of the housing part 5 in such a way that in open position of the speaking valve 1, they are basically arranged above the closure part 4 of the controller 3.

Figure 2:
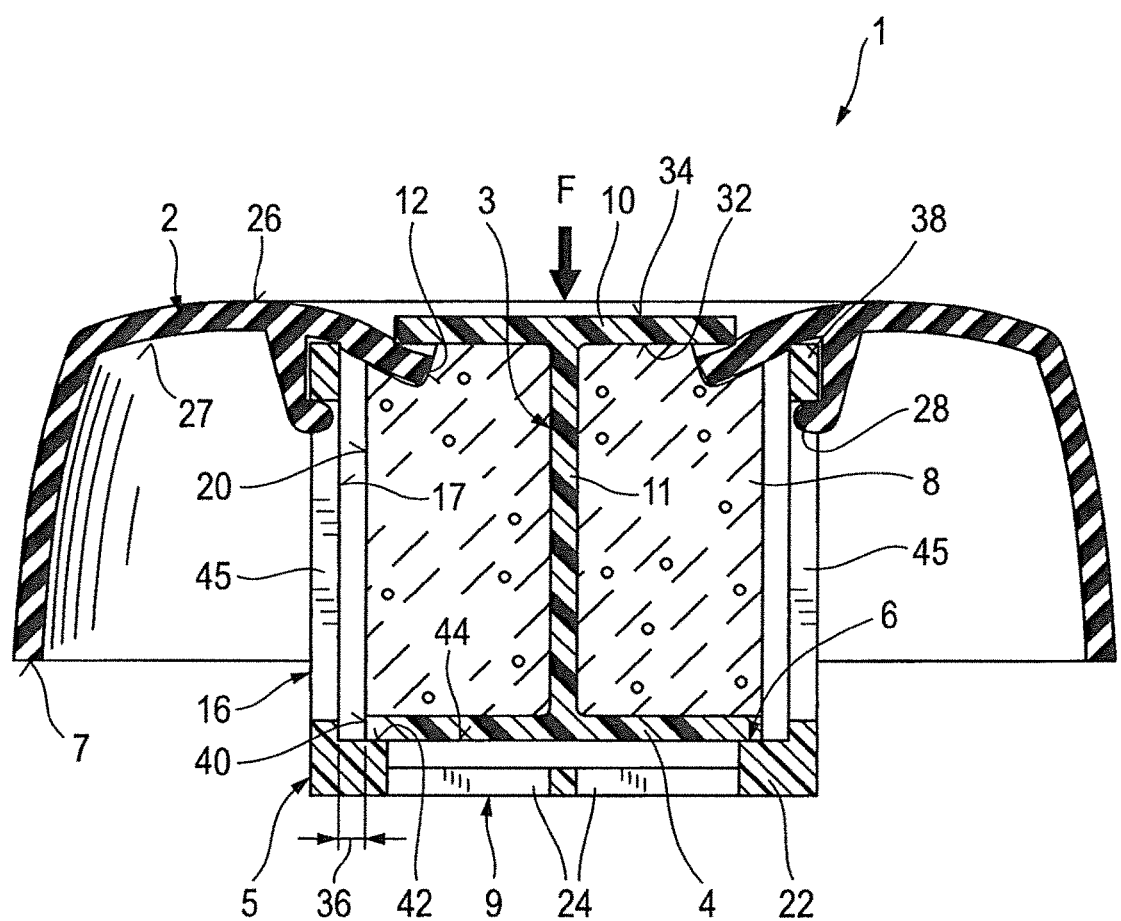
FIG. 2 a lateral sectional view of the speaking valve shown in FIG. 1 in closed position.

FIG. 2 shows the speaking valve 1 shown in FIG. 1 in closed position. To activate the speaking valve 1, a force F is exerted in open position on the cover part 2 or on the mounting element 10 of the cover part, as is shown in FIG. 1. As a result, the elastic cover part 2 is deformed and the controller 3 is moved in the housing part 5 in such a way that the closure part 4 cooperate with the valve seat 6 and closes the speaking valve 1. When the speaking valve 1 is closed, air from exhaling can no longer flow through the outflow opening 9 to the outside and is therefore guided past the vocal cords of the user or the artificial vocal cords of the user to enable speaking.

When the force F acting on the cover part 2 to confirm the controller 3 is released, the controller 3 or the closure part 4 is reset. The resetting forces are caused by the rubber-elastic material of the cover part 2, possibly supplemented in a geometric respect by the form of the cover part 2. In particular, the material and form of the cover part 2 are designed in such a way that the speaking valve 1 can be comfortably closed without exerting too much pressure on the speaking valve 1, which could result in a displacement of the tracheal tube. It is also adjusted in such a way that it is possible to securely reset the speaking valve 1 when the force acting on the cover part 2 is released.

The embodiment shown in FIG. 2 depicts the speaking vale 1 shown in FIG. 1 without the adhesive joint 43. Instead, the cover part 2 is clamped to the mounting element 10 of the cover part. On the one hand, the clamping effect can be achieved in that the mounting element 10 of the cover part has lugs (not shown), which are clamped under the cover part 2. On the other hand, a clamping effect can also be achieved when the cover part 2 is clamped between the mounting element 10 of the cover part and the filter 8.

In the embodiment shown in FIGS. 1 and 2, the filter 8 is in closed position only minimally compressed by the cover part 2. Alternatively, in order to prevent any compression of the filter 8, the cover part 2 can be arranged in such a way that it is arranged, for example by adhesion, at the bottom side of a distal surface 34 of the mounting element 10 of the cover part. At the same time, the arrangement can be made only in an edge region of the cover part 2, or the cover part 2 can overlap the entire mounting element of the cover part. Then the diameter of the mounting element of the cover part can also have a smaller design, or can even be omitted, so that the bottom side 27 of the cover part 2 is connected with the connection piece 11 of the control element 5.

In a further embodiment, it can be especially arranged that the proximal opening 9 has a smaller diameter so that correspondingly also the closure part 4 has a smaller diameter. However, the filter body 20 can maintain its diameter, as shown in FIGS. 1 and 2, so that it protrudes over the side edge 40 of the closure part 4 and, in this way, provides an excellent moisture and heat exchange function. Correspondingly, in such an embodiment, the base 22 would be designed with a wide circumferential edge 44 and, in this case, it would also be possible to omit the reinforcement bars 24 inside he proximal opening 9.

Figure 3:
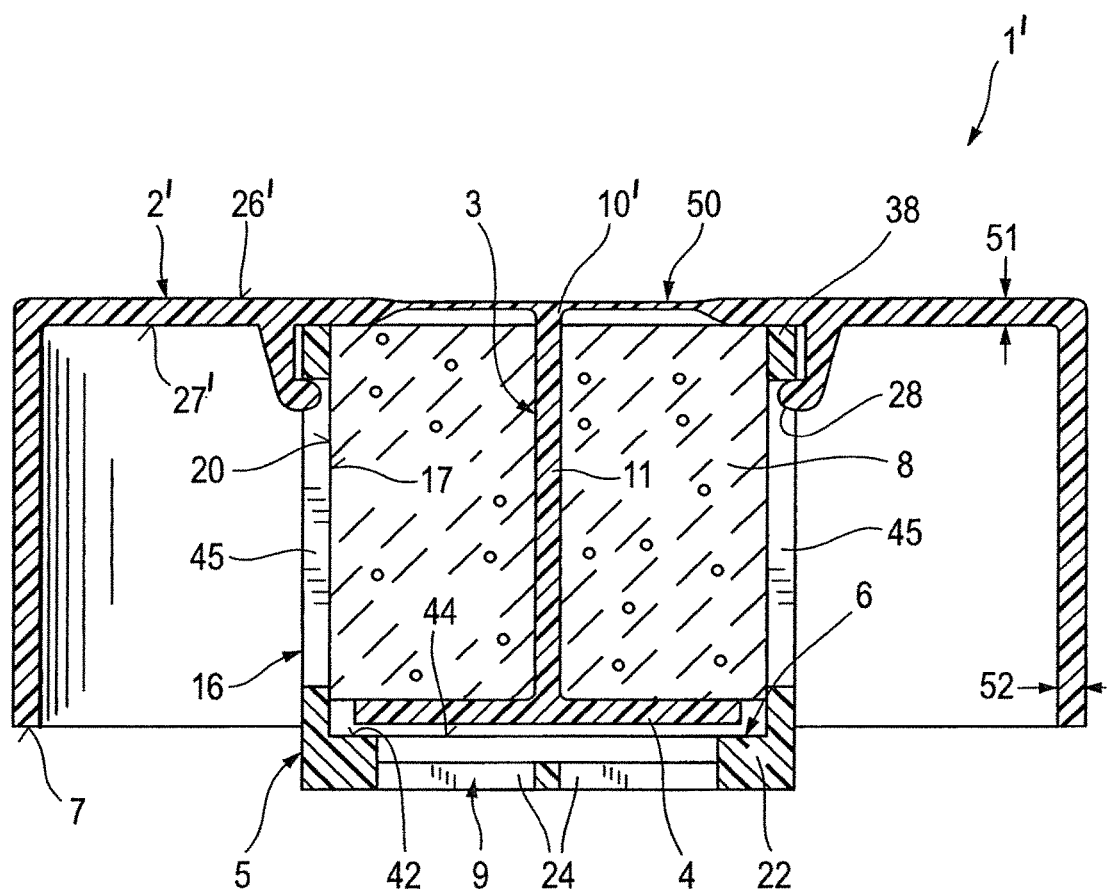
FIG. 3 a lateral sectional view of a further embodiment of the speaking valve in open position.

FIG. 3 shows a further embodiment of the speaking valve in open position in a lateral sectional view. The speaking valve 1' differs from the embodiment shown in FIGS. 1 and 2 in that the cover part 2' and the controller 3 are designed in one piece. In portion 10', the cover part 2' merges into the controller 3. In the transition portion 10', the wall thickness of the cover part 2' is reduced, especially to simplify the handling of the speaking valve 1'. Preferably, controller 3 and cover part 2' are produced from the same material. Said material is semi-rigid, i.e., it has sufficient stability, for example, to press with appropriate pressure the closure part 4 on the valve seat 6, without bending the connection piece 11. Furthermore, the material is flexible enough that a sufficient deformation performed by the force F of a user (shown in FIG. 4) indents the cover part 2' at the material-reduced place so that the controller 3 moves the closure part 4 into a closed position (shown in FIG. 4). In particular, the region of transition 10' is designed in the form of a membrane 50 so that the material can be dented with minimum effort 11. Furthermore, the material is so elastic that it exerts a resetting force on the controller which allows the closure part 4 to be automatically reset into open position. Preferably, the material comprises a medical silicone.

Furthermore, the distal wall thickness 51 of the cover part 2' differs from its cervical wall thickness 52. In particular, the wall thickness 51 of the cover part 2' is larger than the cervical wall thickness 52. Like in the first embodiment, it is connected via lugs 28 arranged at a bottom side 27' with the housing 5.

Figure 4:
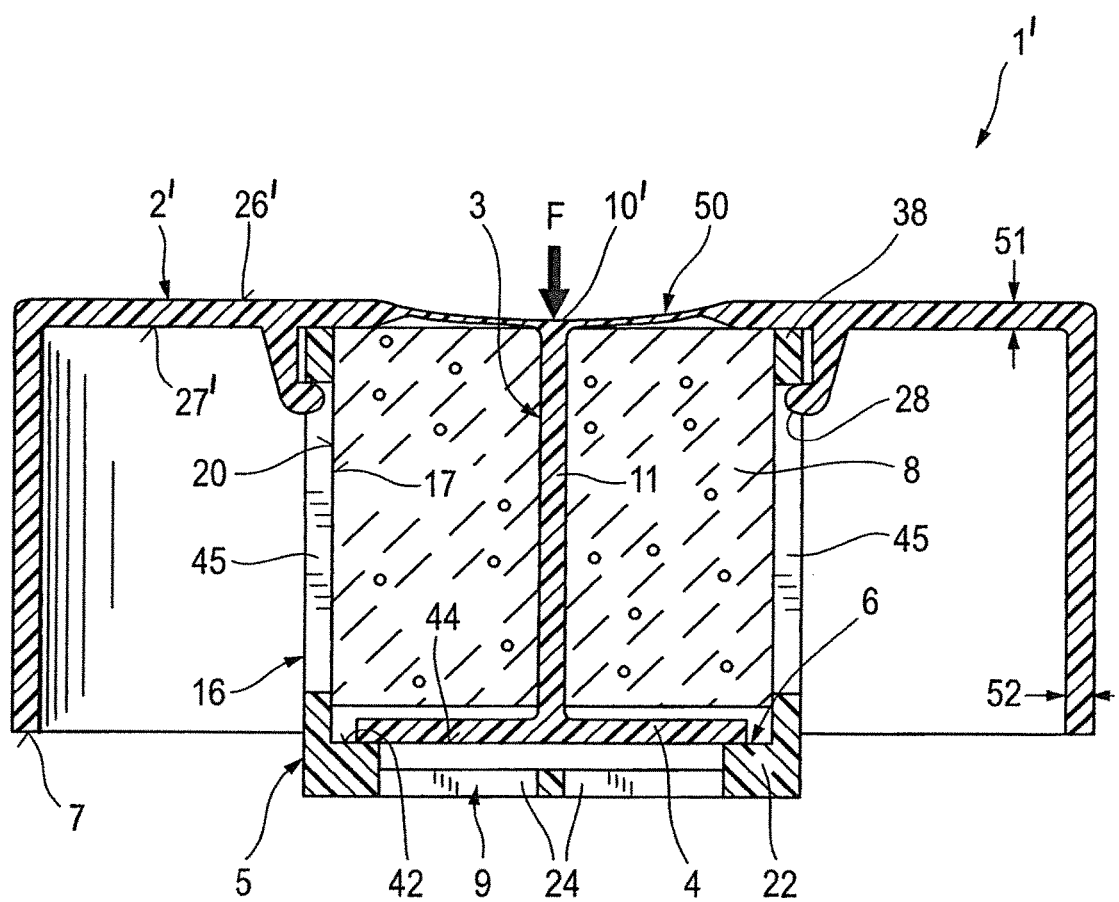
FIG. 4 a lateral sectional view of the speaking valve shown in FIG. 3 in closed position.

FIG. 4 shows a lateral sectional view of the speaking valve depicted in FIG. 3 in closed position. A force F is exerted on the membrane 50, which indents the membrane 50 and thus proximally displaces the connection piece 11 or closure part 4. The embodiment shown depicts that the connection piece 11 moves in relation to the filter 8, wherein also the filter 8 can be moving. In particular, this is achieved in that the filter 8 fits precisely or with an interference fit into the housing 5. The connection piece 11 moves through the opening of the filter 8 and is not connected with the filter 8. By means of the embodiment shown, it is prevented that the activation of the speaking valve 1' puts the filter 8 under strong compression. For this purpose, it is also provided that distally of the filter 8 a clearance is made available between filter 8 and cover part 2', which has an expansion that is larger or equal to the movement range of the valve seat 6. If the space or clearance between closure part 4 and edge 44 is larger, an increase of the force F would result in the fact that the filter 8 would follow the movement of the controller 3, possibly with low compression.

The attachment of the cover part 2' at the upper edge 38 of the housing part 5 is performed analogous to the embodiment of the speaking valve shown in FIGS. 1 and 2.

By means of the present invention, an extremely simple speaking valve is provided, which can be produced from three or four components having a simple design, namely a filter, a controller, a cover part (possibly produced in one piece with the controller) and a housing part. The elasticity required for a resetting process is provided by the cover part. There are no spring elements or the like. In addition, because of the multiple possibilities of designing the cover part with respect to preheating the air and with respect to a non-compression of the filter body to prevent large amounts of moisture from being discharged from the filter, the invention-based speaking valve can have several other advantages.

The invention claimed is:

1. A speaking valve for laryngectomy or tracheostomy care comprising: a cover part, a controller, a housing part and a filter, the housing having an upper edge at one end and forming a valve seat at an opposite end, the cover is mounted to the housing to overlap the upper edge of the housing wherein the controller has a closure part spaced apart from the cover part, the entire filter extending between the closure part and the cover part and wherein the closure part cooperates with the valve seat when the speaking valve is moved from an open position into a closed position, wherein the cover part is formed at least partially from an elastic material, wherein an at least partial deformation takes place at least in a region of the cover part when the speaking valve is moved from an open position into a closed position, and wherein the filter is arranged on the controller in such a way that the filter can follow the movement of the controller within the housing between the open position and the closed position.

2. A speaking valve according to claim 1, wherein the controller is arranged on the cover part.

3. A speaking valve according to claim 1, wherein at least one deformable region of the cover part functions as a resetting means for performing a movement from the closed position into the open position.

4. A speaking valve according to claim 1, wherein the elastic material of the cover part consists of a rubber-elastic material.

5. A speaking valve according to claim 1, wherein the elastic material of the cover part consists of a linear-elastic material.

6. A speaking valve according to claim 1, wherein the cover part consists of an elastic material.

7. A speaking valve according to claim 1, wherein the cover part overlaps at least partially a sidewall of the housing part.

8. A speaking valve according to claim 1, wherein the cover part comprises a height in distal direction which is at least 30% of a height of the housing part.

9. A speaking valve according to claim 1, wherein the cover part laterally and vertically overlaps the housing part.

10. A speaking valve according to claim 1, wherein the cover part has a cervical edge.

11. A speaking valve according to claim 1, wherein the cover part is detachably connected with the housing part and/or the controller.

12. A speaking valve according to claim 1, wherein the cover part is attached to the housing part by means of a snap-on connection.

13. A speaking valve according to claim 1, wherein the housing part comprises at least one inflow opening at a sidewall.

14. A speaking valve according to claim 13, wherein the at least one inflow opening has a lateral expansion, equal a specific height of the filter.

15. A speaking valve according to claim 1, wherein the housing part and/or the controller consist of a rigid material.

16. A speaking valve according to claim 1, wherein the controller comprises at least the closure part, a mounting element of the cover part and a connection piece.

17. A speaking valve for laryngectomy or tracheostomy care comprising: a cover part, a controller, a housing part and a filter, wherein the housing part forms a valve seat, which is proximally arranged in the housing part, the housing part having a side wall having at least one inflow opening having a lateral expansion equal to a specific height of the filter wherein the controller has a closure part spaced apart from the cover part and wherein the closure part cooperates with the valve seat when the speaking valve is moved from an open position into a closed position, wherein the cover part is formed at least partially from an elastic material, wherein an at least partial deformation takes place at least in a region of the cover part when the speaking valve is moved from an open position into a closed position, and wherein the filter is arranged on the controller in such a way that the filter can follow the movement of the controller within the housing between the open position and closed position.

* * * * *